United States Patent [19]

Gadwood

[11] Patent Number: 5,430,048
[45] Date of Patent: Jul. 4, 1995

[54] SPIROCYCLIC BENZOPYRAN IMIDAZOLINES

[75] Inventor: Robert C. Gadwood, Kalamazoo, Mich.

[73] Assignee: The Upjohn Company, Kalamazoo, Mich.

[21] Appl. No.: 194,660

[22] Filed: Feb. 10, 1994

Related U.S. Application Data

[63] Continuation-in-part of Ser. No. 750,596, Aug. 28, 1991, abandoned.

[51] Int. Cl.⁶ .................. A61K 31/415; C07D 491/107
[52] U.S. Cl. .................................... 514/386; 514/402; 548/301.1
[58] Field of Search ............................... 514/386, 402; 548/301.1

[56] References Cited

U.S. PATENT DOCUMENTS 4,740,517 8/1988 Kurono et al. .................. 514/389
4,874,869 10/1989 Ueda et al. .................... 548/309

FOREIGN PATENT DOCUMENTS 057932  8/1982  European Pat. Off. .
193415  9/1986  European Pat. Off. .
344747 12/1989  European Pat. Off. .

*Primary Examiner*—Patricia L. Morris
*Attorney, Agent, or Firm*—Donald L. Corneglio

[57] ABSTRACT

Spiro-[4H-1-benzopyran-4,4'-5'H-imidazol]-5'-ones of the Formula 1:

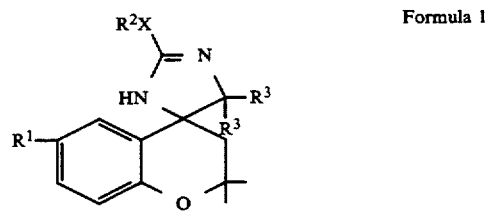

Formula 1 wherein $R^1$ is H, $R^2$ F, Cl, Br, $CF_3$, $CF_3O$, CN, $NO_2$, $R^2SO_2$, $R^2NHSO_2$, $R^2O$, $R^2CO$, $R^2OCO$, or $R^2NHCO$. $R^2$ is a $C_1$–$C_{10}$ branched or linear alkyl, a $C_{3-8}$ cycloalkyl, phenyl, or benzyl. X can be S, O, or NH. Both enantiomers are included in this invention as well as salts and tautomeric forms of these compounds. The subject compounds are useful in the treatment of hypertension, alopecia, and erectile dysfunction.

10 Claims, No Drawings

SPIROCYCLIC BENZOPYRAN IMIDAZOLINES

This application is a continuation of International Patent Application No. PCT/US92/06291, filed Aug. 3, 1992 which is a continuation-in-part of U.S. Ser. No. 07/750,596, filed Aug. 28, 1991, now abandoned.

BACKGROUND OF THE INVENTION

The present invention is directed toward spirocyclic benzopyran imidazolines of Formula shown below, and their use for treatment of hypertension, alopecia, and erectile dysfunction. The subject compounds act by opening cell membrane potassium channels in similar fashion to other known agents such as pinacidil (N-cyano-N'-(4-pyridyl)-N''-(1,2,2-trimethylpropyl)guanidine) and cromakalim ((±)-trans-6-cyano-3,4-dihydro-2,2-dimethyl-4-(2-oxopyrrolidin-1-yl)-2H-1-benzopyran-3-ol). Pinacidil and its analogues are described by H. J. Petersen, et al in *J. Med. Chem.*, 21, 773–781 (1978) and in U.S. Pat. No. 4,057,636. Cromakalim and its analogues are reported by V. A. Ashwood, et al, in *J. Med. Chem.* 29, 2194–2201, (1986) and in European Patent EP 76-075 B. Pinacidil and cromakalim are considered as standard potassium channel openers against which new compounds are compared. The compounds of the present invention are surprisingly more active at relaxing vascular smooth muscle than either pinacidil or cromakalim.

Since potassium channel openers have been shown to have relaxant activity in several types of smooth muscle, the compounds of this invention will be useful for treatment of hypertension, asthma, incontinence, premature labor, and erectile dysfunction. In addition, based on results with other potassium channel openers, the compounds of this invention will have activity as hair growth stimulants and will be useful for treatment of alopecia.

INFORMATION DISCLOSURE STATEMENT

U.S. Pat. No. 4,874,869 discloses a hydantoin derivative which is useful as an intermediate in the preparation of the subject compounds but does not disclose such preparation or compounds.

U.S. Pat. Nos. 4,874,869 and 4,740,517 disclose hydantoin derivatives and spiro-3-heterozolidine compounds, respectively, which are only cited to show the state of the art.

SUMMARY OF THE INVENTION

In one aspect the present invention is a compound of Formula 1 and its pharmaceutically acceptable salts thereof

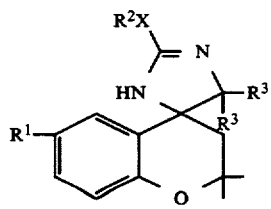

Formula 1 wherein $R^1$ is H, $R^2$, F, Cl, Br, $CF_3$, $CF_3O$, CN, $NO_2$, $R^2SO_2$, $R^2NHSO_2$, $R^2O$, $R^2CO$, $R^2OCO$, or $R^2NHCO$; $R^2$ is linear or branched $C_1$–$C_{10}$ alkyl, a $C_3$–$C_8$ cycloalkyl, phenyl, or benzyl; $R^3$ is H or both $R^3$ together are a double bond to oxygen; and X is S, O, or NH.

In another aspect, the subject invention is the use of a compound of Formula 1 in a method for treatment of hypertension by administering an effective amount to a patient suffering from hypertension. The compound of Formula 1 can also be useful in the treatment of male impotence by direct injection or administration of an effective amount to a male suffering from penile dysfunction.

In yet another aspect, the subject invention is directed toward a method for promoting hair growth comprising the topical administration of an effective amount of a compound of Formula 1 or its pharmaceutically acceptable salts. The method comprises the application of an effective amount of Formula 1 to promote hair growth. Typically, amounts range from about 0.01 to about 20, preferably, 0.5 to 5, more preferably 1 to 3 percent by weight of a compound of Formula 1 are applied.

The method can also comprise the application of an effective amount of such compound admixed in a pharmaceutical carrier adapted for topical application. In another aspect the method includes the routine application of such compound to an area of treatment. Further the routine application can comprise a plurality of treatments such as, for example, daily or twice daily to promote hair growth.

DETAILED DESCRIPTION OF THE INVENTION

The present invention is compounds of Formula 1 and pharmaceutically acceptable acid addition salts as structurally depicted above. The compounds of Formula 1 include both enantiomers as well as salts and tautomeric forms.

Pharmaceutically acceptable acid addition salts of the Formula 1, may be chosen from the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, rosylate, and undecanoate.

The carbon content of various hydrocarbon containing moieties is indicated by a prefix designating the minimum and maximum number of carbon atoms in the moiety, i.e., the prefix $C_i$–$C_j$ indicates a carbon atoms content of the integer "i" to the integer "j" carbon atoms, inclusive. Thus, $C_1$–$C_3$ alkyl refers to alkyl of 1–3 carbon atoms, inclusive, or methyl, ethyl, propyl, and isopropyl, and isomeric forms thereof.

With respect to the above, $C_1$–$C_{10}$ alkyl is methyl, ethyl, propyl, butyl, pentyl, hexyl, heptyl, octyl, nonyl, decyl and isomeric forms thereof (branched and linear). $C_3$–$C_8$ cycloalkyl is cyclopropane, cyclobutane, cyclopentane, cyclohexane, cycloheptane, cyclooctane and isomeric forms thereof.

Preferred compounds of Formula 1 are described below. 2,2-Dimethyl-2'-ethoxy-2,3,3',4'-tetrahydrospiro-[4H-1-benzopyran-4,4'-5'H-imidazol ]-5'one. (Formula 1, $R^1$=H, $R^2$=$CH_2CH_3$, X=O);

6-Bromo-2,2-Dimethyl-2'-ethoxy-2,3,3',4'-tetrahydro-spiro-[4H-1-benzopyran-4,4'- 5'H-imidazol]-5'one. (Formula 1, $R^1$=Br, $R^2$=$CH_2CH_3$, X=O);

2,2-Dimethyl-2'-ethoxy-6-fluoro-2,3,3',4'-tetrahydro-spiro-[4H-1-benzopyran-4,4'-5'H-imidazol]-5'one. (Formula 1, $R^1$=F, $R^2$=$CH_2CH_3$, X=O);

2,2-Dimethyl-2'-propylamino-2,3,3',4'-tetrahydro-spiro-[4H-1-benzopyran-4,4'-5'H-imidazol]-5'one. (Formula 1, $R^1$=H, $R^2$=$CH_2CH_2CH_3$, X=O);

2,2-Dimethyl-2'-(1-methyl)ethylamino-2,3,3',4'-tetrahydro-spiro-[4H-1-benzopyran-4,4'-5'H-imidazol]-5'one. (Formula 1, $R^1$=H, $R^2$=$CH(CH_3)_2$, X=NH);

2,2-Dimethyl-2'-(2,2-dimethyl)propylamino-2,3,3',4'-tetrahydro-spiro-[4H-1-benzopyran-4,4'-5'H-imidazol]-5'one. (Formula 1, $R^1$=H, $R^2$=$CH_2C(CH_3)_3$, X=NH);

6-Bromo-2,2-dimethyl-2'-methylamino-2,3,3',4'-tetrahydro-spiro-[4H-1-benzopyran-4,4'-5'H-imidazol]-5'one. (Formula 1, $R^1$=Br, $R^2$=$CH_3$, X=NH);

6-Bromo-2,2-dimethyl-2'-ethylamino-2,3,3',4'-tetrahydro-spiro-[4H-1-benzopyran -4,4'-5'H-imidazol]-5'one. (Formula 1, $R^1$=Br, $R^2$=$CH_2CH_3$, X=NH);

6-Bromo-2,2-dimethyl-2'-propylamino-2,3,3',4'-tetrahydro-spiro-[4H-1-benzopyran-4,4'-5'H-imidazol-5'one. (Formula 1, $R^1$=Br, $R^2$=$CH_2CH_2CH_3$, X=NH);

6-Bromo-2,2-dimethyl-2'-(1-methyl)ethylamino-2,3,3',4'-tetrahydro-spiro-[4H-1-benzopyran-4,4'-5'H-imidazol]-5'one. (Formula 1, $R^1$=Br, $R^2$=$CH(CH_3)_2$, X=NH);

2,2-Dimethyl-6-fluoro-2'-methylamino-2,3,3',4'-tetrahydro-spiro-[4H-1-benzopyran-4,4'-5'H-imidazol]-5'one. (Formula 1, $R^1$=F, $R^2$=$CH_3$, X=NH);

2,2-Dimethyl-2'-ethylamino-6-fluoro-2,3,3',4'-tetrahydro-spiro-[4H-1-benzopyran-4,4'-5'H-imidazol]-5'one. (Formula 1, $R^1$=F, $R^2$=$CH_2CH_3$, X=NH);

2,2-Dimethyl-6-fluoro-2'-propylamino-2,3,3',4'-tetrahydro-spiro-[4H-1-benzopyran-4,4'-5'H-imidazol]-5'one. (Formula 1, $R^1$=F, $R^2$=$CH_2CH_2CH_3$, X=NH); and 2,2-Dimethyl-6-fluoro-2'-(1-methyl)ethylamino-2,3,3',4'-tetrahydro-spiro-[4H-1-benzopyran-4,4'-5'H-imidazol]-5'one. (Formula 1, $R^1$=F, $R^2$=$CH(CH_3)_2$, X=NH).

The compounds of Formula 1 are useful in the treatment of hypertension and as potassium channel openers. The Formula 1 compounds have been shown to have potent hypotensive activity in normotensive rats. For treatment of hypertension, these compounds can be administered orally in dosages of from 0.01 mg/kg to 10 mg/kg.

The compounds can be administered intravenously, intramuscularly, topically, transdermally such as by skin patches, bucally or orally to man or other animals. The compositions of the present invention can be presented for administration to humans and animals in unit dosage forms, such as tablets, capsules, pills, powders, granules, sterile parenteral solutions or suspensions, oral solutions or suspensions, oil in water and water in oil emulsions containing suitable quantities of the compound, suppositories and in fluid suspensions or solutions.

For oral administration, either solid or fluid unit dosage forms can be prepared. For preparing solid compositions such as tablets, the compound can be mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other insert oil.

Fluid unit dosage forms for oral administration such as syrups, elixirs, and suspensions can be prepared. The forms can be dissolved in an aqueous vehicle together with sugar, aromatic flavoring agents and preservatives to form a syrup. Suspensions can be prepared with an aqueous vehicle with the aid of a suspending agent such as acacia, tragacanth, methylcellulose and the like.

For parenteral administration, fluid unit dosage forms can be prepared utilizing the compound and a sterile vehicle. In preparing solutions the compound can be dissolved in water for injection and filter sterilized before filling into a suitable vial or ampoule and sealing. Adjuvants such as a local anesthetic, preservative and buffering agents can be dissolved in the vehicle. The composition can be frozen after filling into a vial and the water removed under vacuum. The dry lyophilized powder can then be sealed in the vial and reconstituted prior to use.

As potassium channel openers, the compounds of Formula 1 can have utility for treatment of erectile dysfunction (male impotence) via penile injection or via topical penile treatment similar to the known use of prostaglandin. For treatment of impotence, these compounds may be administered via penile injection in quantities of 0.01 to 10.0 mg in an aqueous solution. Alternatively, they may be applied topically to the penis in the same vehicles and concentrations as described for treatment of alopecia.

Also, as potassium channel openers, the Formula 1 compounds have utility as hair growth stimulants when applied topically in a suitable vehicle. In a method for promoting hair growth, the Formula 1 compound is applied to mammalian skin in an effective amount whereby hair growth is promoted. Promotion of hair growth is where the growth of hair is induced or stimulated or where the loss of hair is decreased. For treatment of alopecia, these compounds can be applied topically to balding areas of the scalp in concentrations from 0.1 to 10% by weight in vehicles such as propylene glycol, ethanol, water, propylene carbonate, or N-methylpyrrolidinone, or combinations of these. Penetration enhancers such as oleyl alcohol in concentrations of 0.1 to 1% by weight may also be employed.

PHARMACOLOGY

Rabbit mesenteric artery assay.

Adult white rabbits were anesthetized with ether and then killed by exsanguination. The superior roesenteric artery was rapidly excised, placed in warm physiologic salt solution (PSS), and cleaned of fat and connective tissue. The vessels were cut into rings 2–3 mm wide and equilibrated for 60 rain at 37 ° C. in PSS at pH 7.3. During this period, 100% $O_2$ was bubbled into the solution. Isometric contractions were measured and recorded on a Grass model 7D polygraph using an isolated tissue bath system. Tissues were allowed to equilibrate at 1 g resting tension for at least one hour and then were contracted with 5 μM norepinephrine. After the norepinephrine was washed out, the tissues were left in PSS at resting tension (1 g) for 1 h at which point a second contraction was induced with 5 μM norepinephrine. The compounds were tested at the plateau of the second norepinephrine contraction.

The compounds of this invention prepared in examples 7, 8, and 9 are more potent in this assay than cromakalim. In addition to these compounds, the compounds of examples 4, 10, and 16 were more potent than pinacidil. The data for relaxation of rabbit mesenteric artery and the comparison with cromakalim and pinacidil are shown below in Table 1.

TABLE 1

| Compound | Conc. (μM) | % Relax. |
|---|---|---|
| Example 4 | 0.1 | 60.9 |
|  | 0.5 | 89.7 |
| Example 6 | 0.5 | 19.5 |
|  | 1.0 | 64.7 |
| Example 7 | 0.01 | 4.1 |
|  | 0.05 | 86.5 |
| Example 8 | 0.01 | 10.5 |
|  | 0.05 | 70.2 |
|  | 0.1 | 88.8 |
| Example 9 | 0.01 | 12.0 |
|  | 0.05 | 65.3 |
|  | 0.1 | 90.8 |
| Example 10 | 0.1 | 54.6 |
|  | 0.5 | 88.2 |
| Example 11 | 1.0 | 12.4 |
|  | 5.0 | 79.3 |
| Example 12 | 1.0 | 20.3 |
|  | 5.0 | 76.8 |
| Example 14 | 0.1 | 5.7 |
|  | 0.5 | 79.0 |
| Example 15 | 0.1 | 29.0 |
|  | 0.5 | 86.9 |
| Example 16 | 0.1 | 76.0 |
|  | 0.5 | 86.9 |
| Example 17 | 1.0 | 2.4 |
|  | 5.0 | 89.1 |
| Pinacidil | 0.1 | 25 |
|  | 0.5 | 80 |
|  | 1.0 | 90 |
| Cromakalim | 0.5 | 87.0 |

In vivo hypotensive activity.

Female Sprague-Dawley rats were CUP (α-chloralose/urethane/pentobarbitol) anethsthetized and placed on a heated, insulated tilt rack. Thirty minutes after anethesia, the rats were removed from the tilt rack to permit cannulation of of the fight external jugular vein and the left common carotid artery with PE-50 catherters. Mean arterial pressure was recorded through the arterial cannula. After surgical preparation, the rats were returned to the tilt rack and then treated i.v. with the test drug. The data for changes in mean arterial pressure after i.v. dosing of CUP-anesthetized rats are shown below in Table 2.

It can be seen that the compound of Example 7 is more potent than cromakalim in this assay, while the compound of example 15 is approximately equal in potency to cromakalim.

TABLE 2

| Compound | Dose (mg/kg) | ΔMAP in Pa (mm Hg) |
|---|---|---|
| Example 7 | 0.01 | −5333 (−40) |
|  | 0.04 | −7999 (−60) |
|  | 0.14 | −9999 (−75) |
| Example 15 | 0.04 | −1999 (−15) |
|  | 0.14 | −3999 (−30) |
|  | 0.44 | −6666 |

TABLE 2-continued

| Compound | Dose (mg/kg) | ΔMAP in Pa (mm Hg) |
|---|---|---|
|  |  | (−50) |
| Cromakalim | 0.04 | −2666 |
|  |  | (−20) |
|  | 0.14 | −3999 |
|  |  | (−30) |
|  | 0.44 | −7333 |
|  |  | (−55) |

A typical method for preparing the compounds of formula 1 where X is O, is by the reaction of a spirocyclic hydantoin of formula 1, where the $R^2X$ group is =O (formula 1'), with a trialkyloxonium tetrafluoroborate reagent such as triethyloxonium tetrafluoroborate. The spirocyclic hydantoins can be prepared by procedures described in detail below which are essentially the same as those described by K. Ueda, et al, in U.S. Pat. No. 4,874,869.

In those compounds of formula 1 where X is S, the compound is prepared by reaction of a spirocyclic thiohydantoin of formula 1, where the $R^2X$ group is =S (formula 1''), with an alkyl iodide such as methyl iodide. Compounds of this formula can in rum be prepared by reaction of the spirocyclic hydantoins of formula 1' with Lawesson's reagent.

In those compounds of formula 1 where X is NH, the compound is prepared by reaction of an alkyl amine such as propyl amine with one of the previously described compounds of formula where X is either O or S.

The subject compounds can be made according to the procedures outlined in the following examples. Where the $R^2X$ group is —OH the formula is designated—Formula 1', and where the $R^2X$ group is —SH the formula is designated—Formula 1''. It is noted, however, that tautomeric forms of Formula 1' and 1'' exist where the —OH and —SH would be =O and =S and the bond between the appropriate carbon and nitrogen atom becomes a single bond to provide a correct valence.

In vivo hair growth activity.

Male rats were randomized into control and treatment groups with six rats per group. One day prior to the beginning of each assay, the lumbodorsal region of the back of each rat was shaved and a 2.54 cm square area was defined by 4 tattoo marks. Each rat was topically dosed with vehicle or test compound (250 μL once per day, 5 days/week, Monday through Friday) in the tattooed area of the back via a 250 μL micropipette. The test compounds were applied in a vehicle of propylene carbonate and N-methylpyrrolidinone. At 7-day intervals during the assay, each animal was anesthetized and the tattooed area was shaved and the hair was collected and weighed. The assay was continued for 4 weeks. The cumulative hair weights are tabulated in Table 3.

TABLE 3

| Compound | Dose (mM) | Hair Weight (mg) | SEM (±mg) |
|---|---|---|---|
| Example 7 | 0.1 | 27.8 | 3.3 |
|  | 1.0 | 38.8* | 7.6 |
| Example 15 | 10 | 35.0* | 6.4 |
|  | 50 | 44.7* | 10.7 |
| Vehicle |  | 20.6 | 4.8 |

*Statistically significant relative to vehicle (p < 0.1).

In vitro erectile stimulation.

Six cynomolgus monkeys were sedated with ketamine. The compound of Example 7 was injected into the corpus cavernosum of each monkey at a dose of 0.75 μg in 0.1% DMSO/saline solution. Five of the six monkeys showed a positive response which was characterized by penile elevation along with rigidity and pulsation.

EXAMPLE 1

Preparation of
2,3-Dihydro-2,2-dimethyl-spiro-[4H-1-benzopyran-4,4'-imidazolidine]-2',5'-dione (Formula 1', $R^1$=H).

A glass pressure tube was charged with a mixture of 2,3-dihydro-2,2-dimethyl-4H-1-benzopyran-4-one (4.4 g, 25 mmol), KCN (5.2 g, 50 mmol) and $(NH_4)_2CO_3$ (16.0 g, 187.5 mmol). Enough formamide was added to fill the pressure tube nearly completely (ca. 100 mL). The mixture was heated at 70° C. for 24 h and then at 110° C. for another 48 h. The reaction mixture was then cooled, poured over ice, and filtered. The filtrate was acidified with conc. HCl and extracted with $CHCl_3$. The combined organic phases were washed with brine, dried with $Na_2SO_4$, and concentrated in vacuo to afford the crude product. Purification on silica gel using 8% methanol/chloroform as eluent afforded 5.0 g of product (82% yield): mp 233°–235° C. (lit mp [U.S. Pat. No. 4,874,869]=24920 –250° C.); $^1$H NMR (DMSO) δ 10.99 (1 H, bs), 8.58 (1 H, s), 7.13 (1 H, td, J=8, 1 Hz), 6.94 (1 H, dd, J=7, 1 Hz), 6.84 (1 H, t, J=7 Hz), 6.71 (1 H, d, J=8 Hz), 2.33 (1, H, HA of AB, $J_{AB}$=14 Hz), 2.15 (1 H, HB of AB, $J_{AB}$=14 Hz), 1.32 (3 H, s), 1.17 (3 H, s); Anal calcd for $C_{13}H_{14}N_2O_3$: C,63.41; H, 5.73; N, 11.38. Found: C, 63.15; H, 6.02; N, 11.16.

EXAMPLE 2

Preparation of
6-Bromo-2,3-dihydro-2,2-dimethyl-spiro[4H-1-benzopyran-4,4'- imidazolidine]-2',5'-dione (Formula 1', $R^1$=Br).

This compound was prepared by the same procedure as described in Example 1. Yield 80%. mp 278°–280° C. (lit mp [U.S. Pat. No. 4,874,869]=299°–300° C.); $^1$H NMR (DMSO) δ 11.15 (1 H, bs), 8.74 (1 H, s), 7.40 (1 H, dd, J=9, 2 Hz), 7.11 (1 H, d, J=2 Hz), 6.81 (1 H, d, J=9 Hz), 2.31 (1 H, HA of AB, $J_{AB}$=14 Hz), 2.18 (1 H, HB of AB, $J_{AB}$=14 Hz), 1.42 (3 H, s), 1.25 (3 H, s); Anal calcd for $C_{13}H_{13}BrN_2O_3$:C, 48.02; H, 4.03; N, 8.62; Br, 24.57. Found: C, 47.90; H, 4.15; N, 8.49; Br, 24.08.

EXAMPLE 3

Preparation of
6-Fluoro-2,3-dihydro-2,2-dimethyl-spiro[4H-1-benzopyran-4,4'-imidazolidine]-2',5'-dione (Formula 1', $R^1$=F).

This compound was prepared by the same procedure as described in Example 1. Yield 72%. mp 275°–277° C. (lit mp [U.S. Pat. No. 4,874,869] 293°–294° C.); $^1$H NMR (DMSO) δ 11.1 (1 H, bs), 8.74 (1 H, s), 7.13 (1 H, td, J=9, 3 Hz), 6.87 (2 H, m), 2.32 (1 H, HA of AB, $J_{AB}$=14 Hz), 2.18 (1 H, HB of AB, $J_{AB}$=14 Hz), 1.43 (3 H, s), 1.27 (3 H, s); Anal calcd for $C_{13}H_{13}FN_2O_3$: C, 59.09; H, 4.96; N, 10.60; F, 7.19. Found: C, 58.62; H, 4.97; N, 10.51; F, 6.98.

EXAMPLE 4

Preparation of
6-Bromo-2,2-dimethyl-2'-ethoxy-2,3,3',4'-tetrahydro-spiro-[4H-1- benzopyran-4,4'-5'H-imidazol]-5'one. (Formula 1, $R^1$=Br, $R^2$=$CH_2CH_3$, X=O).

To a suspension of the hydantoin of example 2 (1.95 g, 6.0 mmol) in 80 mL of $CH_2Cl_2$ was added at room temperature under $N_2$ a solution of triethyloxonium tetrafluoroborate (1M in $CH_2Cl_2$, 12 mL, 12 mmol). The resulting suspension was heated to reflux for 60 h. The reaction was cooled to room temperature, diluted with 80 mL of $CH_2Cl_2$ and neutralized with 10% aqueous $NaHCO_3$. The organic layer was separated, dried ($Na_2SO_4$), filtered, and concentrated in vacuo to afford a yellow solid. Purification on silica gel using 4% $CH_3OH/CHCl_3$ as eluent gave 1.2 g (57% yield) of the product: mp 182°–184° C.; $^1$H NMR ($CDCl_3$) δ 7.29 (1 H, dd, J=9, 2 Hz), 7.0 (1 H, d, J=2 Hz), 6.72 (1 H, d, J=9 Hz), 6.45 (1 H, bs), 4.36 (2 H, q, J=7 Hz), 2.55 (1 H, d, J=14 Hz), 1.98 (1 H, d, J=14 Hz), 1.48 (3 H, s), 1.43 (3 H, t, J=7 Hz), 1.27 (3 H, s); Anal Calc'd for $C_{15}H_{17}BrN_2O_3$: C, 51.00; H, 4.85; N, 7.93; Br, 22.62. Found: C, 50.69; H, 5.18; N, 7.76; Br, 21.40.

EXAMPLE 5

Preparation of
2,2-Dimethyl2'-ethoxy-2,3,3',4'-tetrahydro-spiro-]4H-1-benzopyran-4,4'-5'H-imidazol]-5'one. (Formula 1, $R^1$=H, $R^2$=$CH_2CH_3$, X=O).

Following the procedure of example 4, this compound was prepared from the hydantoin of example 1 in 85% yield: mp 153°–155° C.; $^1$H NMR ($CDCl_3$) δ 7.22 (1 H, m), 6.87 (3 H, m), 5.25 (1 H, bs), 4.63 (2 H, q, J=7 Hz), 2.60 (1 H, d, J=14 Hz), 1.98 (1 H, d, J=14 Hz), 1.49 (3 H, s), 1.45 (3 H, t, J=7 Hz), 1.30 (3 H, s); Anal calcd for $C_{15}H_{18}N_2O_3$: C, 65.68; H 6.61; N, 10.21. Found: C, 65.01; H, 6.57; N, 10.16.

EXAMPLE 6

Preparation of
2,2-Dimethyl-2'-ethoxy-6-fluoro-2,3,3',4'-tetrahydro-spiro-[4H-1-benzopyran-4,4'-5'H-imidazol]-5'one. (Formula 1, $R^1$=F, $R^2$=$CH_2CH_3$, X=O).

Following the procedure of example 4, this compound was prepared from the hydantoin of example 1 in 60% yield. mp 209°–211° C.; $^1$H NMR ($CDCl_3$) δ 6.90 (1 H, td, J=9, 3 Hz), 6.75 (1 H, dd, J=9, 5 Hz), 6.61 (1 H, dd, J=9, 3 Hz), 4.59 (2 H, q, J=7 Hz), 2.50 (1 H, d, J=14 Hz), 2.10 (1 H, d, J=14 Hz), 1.48 (3 H, s), 1.43 (3 H, t, J=7 Hz), 1.28 (3 H, s). Anal calcd for $C_{15}H_{17}FN_2O_3$: C, 61.63; H, 5.86; N, 9.58; F, 6.50. Found: C, 61.40; H, 5.86; N, 9.50; F, 5.89.

EXAMPLE 7

Preparation of
6-Bromo-2,2-dimethyl-2'-propylamino-2,3,3',4'-tetrahydro-spiro- [4H-1-benzopyran-4,4'-5'H-imidazol]-5'one. (Formula 1, $R^1$=Br, $R^2$=$CH_2CH_2CH_3$, X=NH).

A solution of the starting material of example 4 (2.75 g, 7.8 mmol) and propyl amine (0.96 g, 16 mmol) in 30 mL of absolute ethanol was refluxed for 18 h. The reaction was then concentrated in vacuo to afford a solid residue which was recrystallized from methanol/ethyl acetate to afford 2.6 g of product (91% yield): mp 225°–227° C.; $^1$H NMR ($CDCl_3$) δ 7.25 (1 H, dr, J=9, 2

Hz), 7.01 (1 H, d, J=2 Hz), 6.71 (1 H, d, J=9 Hz), 3.38 (2 H, t, J=8 Hz), 2.47 (1 H, d, J=14 Hz), 1.94 (1 H, d, J=14 Hz), 1.63 (2 H, sextet, J=7 Hz), 1.48 (3 H, s), 1.27 (3 H, s), 0.98 (3 H, t, J=7 Hz). Anal calcd for $C_{16}H_{20}BrN_3O_2$: C, 52.47; H, 5.50; N, 11.47; Br, 21,82. Found: C, 52.44; H, 5.47; N, 11.00; Br, 20.80.

EXAMPLE 8

Preparation of 6-Bromo-2,2-dimethyl-2'-ethylamino-2,3,3',4'-tetrahydro-spiro-]4H-1-benzopyran-4,4'-5'H-imidazol]-5'one. (Formula 1, $R^1$=Br, $R^2$=$CH_2CH_3$, X=NH)

This compound was prepared from the starting material of example 4 and ethylamine according to the procedure described in example 7 in 60% yield: mp 277°–279° C.; $^1$H NMR (CD$_3$OD) δ 7.26 (1 H, dd, J=9, 2 Hz), 7.01 (1 H, d, J=2 Hz), 6.21 (1 H, d, J=9 Hz), 3.43 (2 H, m), 2.46 (1 H, d, J=14 Hz), 1.94 (1 H, d, J=14 Hz), 1.48 (3 H, s), 1.27 (3 H, s), 1.24 (3 H, t, J=7 Hz). Anal calcd for $C_{15}H_{18}BrN_3O_2$: C, 51.15; H, 5.15; N, 11.93; Br, 22.69. Found: C, 49.38; H, 4.91; N, 11.52; Br, 22.52.

EXAMPLE 9

Preparation of 6-Bromo-2,2-dimethyl-2'-methylamino-2,3,3',4'-tetrahydro-spiro-[4H-1-benzopyran-4,4'-5'H-imidazol]-5'one. (Formula 1, $R^1$=Br, $R^2$=$CH_3$, X=NH).

This compound was prepared from the starting material of example 4 and methylamine according to the procedure described in example 7 in 77% yield: mp>300° C.; $^1$H NMR (CD$_3$OH) δ 7.27 (1 H, dd, J=9, 2 Hz), 7.03 (1 H, d, J=2 Hz), 6.72 (1 H, d, J=9 Hz), 3.05 (3 H, s) 2.47 (1 H, d, J=14 Hz), 1.96 (1 H, d, J=14 Hz), 1.49 (3 H, s), 1.29 (3 H, S). Anal calcd for $C_{14}H_{16}BrN_3O_2$: C, 49.72; H, 4.77; N, 12.42; Br, 23.63. Found: C, 49.51; H, 4.74; N, 12.33; Br, 23.25.

EXAMPLE 10

Preparation of 6-Bromo-2,2-dimethyl-2'-(1-methyl)ethylamino-2,3,3',4'-tetrahydro-spiro-[4H-1-benzopyran-4,4'-5'H-imidazol]-5'one. (Formula 1, $R^1$=Br, $R^2$=CH(CH$_3$)$_2$, X=NH).

This compound was prepared from the staging material of example 4 and isopropylamine according to the procedure described in example 7 in 48% yield: mp 235°–237° C. $^1$H NMR (CDCl$_3$) δ 8.44 (1 H, s), 7.63 (1 H), 7.20 (1 H, dd, J=9, 2 Hz), 6.90 (1 H, d, J=2 Hz), 6.65 (1 H, d, J=9 Hz), 3.49 (1 H, septet, J=7 Hz), 2.33 (1 H, d, J=14 Hz), 1.85 (1 H, d, J=14 Hz), 1.40 (3 H, s), 1.18 (3 H, s), 1.02 (3 H, d, J=7 Hz). Anal calcd for $C_{16}H_{20}BrN_3O_2$: C, 52.47; H, 5.50; N, 11.47; Br, 21.82. Found: C, 52.01; H, 5.42; N, 11.30; Br, 21.07.

EXAMPLE 11

Preparation of 2,2-Dimethyl-2'-propylamino-2,3,3',4'-tetrahydro-spiro-[4H-1- benzopyran-4,4'-5'H-imidazol]-5'one. (Formula 1, $R^1$=H, $R^2$=$CH_2CH_2CH_3$, X=NH).

This compound was prepared from the starting material of example 5 and propylamine according to the procedure of example 7 in 92% yield: mp 205°–207° C.; $^1$H NMR (CDCl$_3$) δ 7.13 (1 H, m), 6.83 (3 H, m), 3.24 (2 H, t, J=7 Hz), 2.45 (1 H, d, J=14 Hz), 1.88 (1 H, d, J=14 Hz), 1.55 (2 H, sextet, J=7 Hz), 1.44 (3 H, s), 1.23 (3 H, s), 0.91 (3 H, t, J=7 Hz); Anal calcd for $C_{16}H_{21}N_3O_2$: C, 66.88; H, 7.37; N, 14.62. Found: C, 66.47; H, 7.51; N, 14.39.

EXAMPLE 12

Preparation of 2,2-Dimethyl-2'-(1-methyl)ethylamino-2,3,3',4'-tetrahydro-spiro-[4H-1-benzopyran-4,4'-5'H-imidazol]-5'one. (Formula 1, $R^1$=H, $R^2$=CH(CH$_3$)$_2$, X=NH)

This compound was prepared from the starting material of example 5 and isopropylamine according to the procedure of example 7 in 54% yield: mp 225°–227° C.; $^1$H NMR (CDCl$_3$) δ 7.12 (1 H, m), 6.81 (3 H, m), 3.83 (1 H, m), 2.40 (1 H, d, J=14 Hz), 1.85 (1 H, d, J=14 Hz), 1.42 (3 H, s), 1.21 (3 H, s), 1.10 (6 H, t, J=5 Hz). Anal calcd for $C_{16}H_{21}N_3O_2$: C, 66.88; H, 7.17; N, 14.62. Found: C, 66.79; H, 7.37; N, 14.60.

EXAMPLE 13

Preparation of 2,2-Dimethyl-2'-(2,2-dimethyl)propylamino-2,3,3',4'-tetrahydro-spiro-[4H-1-benzopyran-4,4'-5'H-imidazol]-5'one. (Formula 1, $R^1$=H, $R^2$=$CH_2C(CH_3)_3$, X=NH).

This compound was prepared from the starting material of example 5 and neopentylamine according to the procedure of example 7 in 55% yield: mp 293°–295° C.; $^1$H NMR (CDCl$_3$) δ 7.15 (1 H, m), 6.82 (3 H, m), 3.33 (1 H, HA of AB, $J_{AB}$=13 Hz), 3.18 (1 H, HB of AB $J_{AB}$=13 Hz), 2.48 (1 H, d, J=14 Hz), 1.90 (1 H, d, J=14 Hz), 1.47 (3 H, s), 1.36 (3 H, s), 0.95 (9 H); Anal calcd for $C_{18}H_{25}N_3O_2$: C, 68.54; H, 7.99; N, 13.32. Found: C, 68.26; H, 7.95; N, 13.18.

EXAMPLE 14

Preparation of 2,2-Dimethyl-6-fluoro-2'-methylamino-2,3,3',4'-tetrahydro-spiro[4H-1-benzopyran-4,4'-5'H-imidazol]-5'one. (Formula 1, $R^1$=F, $R^2$=$CH_3$, X=NH).

This compound was prepared from the starting material of example 6 and methylamine according to the procedure of example 7 in 95% yield: mp 283°–285° C.; $^1$H NMR (CDCl$_3$) δ 6.86 (1 H, td, J=9, 3 Hz), 6.75 (1 H, dd, J=9, 5 Hz), 6.60 (1 H, dd, J=9, 3 Hz), 2.93 (3 H, S), 2.42 (1 H, d, J=14 Hz), 1.90 (1H, d, J=14 Hz), 1.44 (3 H, s), 1.22 (3 H, s); Anal calcd for $C_{14}H_{16}FN_3O_2$: C, 60.64; H, 5.82; N, 15.15; F, 6.85. Found: C, 60.14; H, 5.77; N, 15.15; F, 5.77.

EXAMPLE 15

Preparation of 2,2-Dimethyl-2'-ethylamino-6-fluoro-2,3,3',4' -tetrahydro-spiro-[4H-1-benzopyran-4,4'-5'H-imidazol]-5'one- (Formula 1, $R^1$=F, $R^2$=$CH_2CH_3$, X=NH).

This compound was prepared from the starting material of example 6 and ethylamine according to the procedure of example 7 in 77% yield: mp 259°–261° C.; $^1$H NMR (CDCl$_3$) δ 6.86 (1 H, td, J=9, 3 Hz), 6.74 (1 H, dd, J=9, 5 Hz), 6.59 (1 H, dd, J=9, 3 Hz), 3.33 (2 H, q, J=7 Hz), 2.22 (1 H, d, J=14 Hz), 1.89 (1 H, d, J=14 Hz), 1.44 (3 H, s), 1.22 (3 H, s), 1.17 (3 H, t, J=7 Hz). Anal calcd for $C_{15}H_{18}FN_3O_2$: C, 61.89; H, 6.23; N, 14.42; F, 6.52. Found: C, 61.84; H, 6.27; N, 14.49; F, 6.78.

EXAMPLE 16

Preparation of
2,2-Dimethyl-6-fluoro-2'-propylamino-2,3,3',4'-tetrahydro-spiro-[4H-1-benzopyran-4,4'-5'H-imidazol]-5'one-
(Formula 1, $R^1=F$, $R^2=CH_2CH_2CH_3$, $X=NH$).

This compound was prepared from the starting material of example 6 and propylamine according to the procedure of example 7 in 65% yield: mp 216°–218° C.; $^1$H NMR (CDCl$_3$) δ 6.84 (1 H, td, J=9, 3 Hz), 6.74 (1 H, dd, J=9, 5 Hz), 6.55 (1 H, dd, J=9, 3 Hz), 3.20 (2 H, q, J=7 Hz), 2.37 (1 H, d, J=14 Hz), 1.86 (1 H, d, J=14 Hz), 1.53 (2 H, sextet, J=7 Hz), 1.42 (3 H, s), 1.19 (3 H, s), 0.90 (3 H, t, J=7 Hz). Anal calcd for $C_{16}H_{20}FN_3O_2$: C, 62.85; H, 6.67; N, 13.48; f, 6.10. Found: C, 62.13; H, 6.62; N, 13.37; F, 6.20.

EXAMPLE 17

Preparation of
2,2-Dimethyl-6-fluoro-2'-(1-methyl)ethylamino-2,3,3',4'-tetrahydro-spiro-[4H-1-benzopyran-4,4'-5'H-imidazol]-5'one-
(Formula 1, $R^1=F$, $R^2=CH(CH_3)_2$, $X=NH$).

This compound was prepared from the starting material of example 6 and isopropylamine according to the procedure of example 7 in 60% yield: mp 261°–262° C.; $^1$H NMR (CDCl$_3$) δ 6.89 (1 H, td, J=9, 3 Hz), 6.77 (1 H, dd, J=9, 5 Hz), 6.6 (1 H, dd, J=9, 3 Hz), 4.06 (1 H, septet), 2.48 (1 H, d, J=14 Hz), 1.92 (1 H, d, J=14 Hz), 1.47 (3 H, s), 1.24 (6 H, d, J=6 Hz), 1.20 (3 H, s). Anal calcd for $C_{16}H_{20}FN_3O_2$: C, 62.94; H, 6.60; N, 13.76; F, 6.22. Found: C, 62.48; H, 6.80; N, 13.57; F, 6.20.

I claim:

1. A compound of Formula 1 and its pharmaceutically acceptable salts thereof

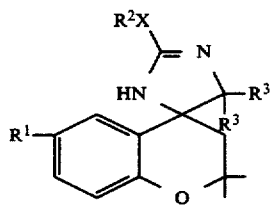

Formula 1 wherein
$R^1$ is H, $R^2$, F, Cl, Br, CF$_3$, CF$_3$O, CN, NO$_2$, $R^2$SO$_2$, $R^2$NHSO$_2$, $R^2$O, $R^2$CO, $R^2$OCO or $R^2$NHCO;
$R^2$ is a $C_1$–$C_{10}$ alkyl, a $C_3$–$C_8$ cycloalkyl, phenyl, or benzyl;
$R^3$ is H or both $R^3$ together are a double bond to oxygen; and
X is S, O, or NH.

2. The compound of claim 1 wherein $R^1$ is a H, Br, or F.
3. The compound of claim 1 wherein X is NH.
4. The compound of claim 1 wherein X is O.
5. The compound of claim 1 which is
a) 2,2-Dimethyl-2'-ethoxy-2,3,3',4'-tetrahydro-spiro-[4H-1-benzopyran-4,4'-5'H-imidazol]-5'one;
b) 6-Bromo-2,2-Dimethyl-2'-ethoxy-2,3,3',4'-tetrahydro-spiro-[4H-1-benzopyran-4,4'-5'H-imidazol]-5'one;
c) 2,2-Dimethyl-2'-ethoxy-6-fluoro-2,3,3',4'-tetrahydro-spiro-[4H-1-benzopyran-4,4'-5'H-imidazol]-5'one;
d) 2,2-Dimethyl-2'-propylamino-2,3,3',4'-tetrahydro-spiro-[4H-1-benzopyran-4,4'-5'H-imidazol]-5'one;
e) 2,2-Dimethyl-2'-(1-methyl)ethylamino-2,3,3',4'-tetrahydro-spiro-[4H-1-benzopyran-4,4'-5'H-imidazol]-5'one;
f) 2,2-Dimethyl-2'-(2,2-dimethyl)propylamino-2,3,3',4'-tetrahydro-spiro-[4H-1-benzopyran-4,4'-5'H-imidazol]-5'one;
g) 6-Bromo-2,2-dimethyl-2'-methylamino-2,3,3',4'-tetrahydro-spiro-[4H-1-benzopyran-4,4'-5'H-imidazol]-5'one;
h) 6-Bromo-2,2-dimethyl-2'-ethylamino-2,3,3',4'-tetrahydro-spiro-[4H-1-benzopyran-4,4'-5'H-imidazol]-5'one;
i) 6-Bromo-2,2-dimethyl-2'-propylamino-2,3,3',4'-tetrahydro-spiro[4H-1-benzopyran-4,4'-5'H-imidazol]-5'one;
j) 6-Bromo-2,2-dimethyl-2'-(1-methyl)ethylamino-2,3,3',4'-tetrahydro-spiro-[4H-1-benzopyran-4,4'-5'H-imidazol]-5'-one;
k) 2,2-Dimethyl-6-fluoro-2'-methylamino-2,3,3',4'-tetrahydro-spiro-[4H-1-benzopyran-4,4'-5'H-imidazol]-5'one;
l) 2,2-Dimethyl-2'-ethylamino-6-fluoro-2,3,3',4'-tetrahydro-spiro-[4H-1-benzopyran-4,4'-5'H-imidazol]-5'one;
m) 2,2-Dimethyl-6-fluoro-2'-propylamino-2,3,3',4'-tetrahydro-spiro-[4H-1-benzopyran-4,4'-5'H-imidazol]-5'one; and
n) 2,2-Dimethyl-6-fluoro-2'-(1-methyl)ethylamino-2,3,3',4'-tetrahydro-spiro-[4H-1-benzopyran-4,4'-5'H-imidazol]-5'one.

6. A method for treating hypertension comprising the administration of a therapeutically effective amount of a compound of Formula 1 or a pharmaceutically acceptable salt thereof to an animal, including humans, suffering therefrom.

7. The method of claim 6 wherein said compound of Formula 1 is administered intravenously, intramuscularly, topically, transdermally, bucally, orally, or parenterally.

8. The method of claim 6 wherein said therapeutically effective amount is from about 0.01 mg/kg to about 10 mg/kg orally.

9. A method for treatment of hair loss comprising the administration of a therapeutically effective amount of a compound of Formula 1 or a pharmaceutically acceptable salt thereof to an animal, including humans, in need thereof.

10. A method of a compound of Formula 1 or a pharmaceutically acceptable salt thereof for treatment of erectile dysfunction comprising the administration of a therapeutically effective amount to an animal, including man, in need thereof.

* * * * *